(12) United States Patent
Gelfand et al.

(10) Patent No.: US 10,518,090 B2
(45) Date of Patent: *Dec. 31, 2019

(54) SYSTEM AND METHOD TO MODULATE PHRENIC NERVE TO PREVENT SLEEP APNEA

(75) Inventors: Mark Gelfand, New York, NY (US); Howard R. Levin, Teaneck, NJ (US); Andrew Halpert, Coral Springs, FL (US)

(73) Assignee: RESPICARDIA, INC., Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/538,713

(22) Filed: Jun. 29, 2012

(65) Prior Publication Data

US 2013/0165989 A1    Jun. 27, 2013

Related U.S. Application Data

(63) Continuation of application No. 11/601,150, filed on Nov. 17, 2006, now Pat. No. 8,244,359.

(51) Int. Cl.
*A61N 1/36*    (2006.01)
*A61N 1/05*    (2006.01)
*A61B 5/08*    (2006.01)

(52) U.S. Cl.
CPC .......... *A61N 1/3611* (2013.01); *A61B 5/0816* (2013.01); *A61B 5/0826* (2013.01); *A61N 1/0551* (2013.01); *A61N 1/3601* (2013.01); *A61N 1/36135* (2013.01)

(58) Field of Classification Search
CPC ............................ A61N 1/3601; A61N 1/3611; A61N 1/36514; A61N 1/3605; A61N 1/0551; A61B 5/08; A61B 5/4818; A61B 5/0205; A61B 5/113; A61B 5/0816; A61B 5/0826
USPC ................. 607/2, 42, 62, 116, 118; 600/372
See application file for complete search history.

(56) References Cited

U.S. PATENT DOCUMENTS

| | | |
|---|---|---|
| 4,129,125 A | 12/1978 | Lester et al. |
| 4,827,935 A | 5/1989 | Geddes et al. |
| 5,056,519 A | 10/1991 | Vince |
| 5,146,918 A | 9/1992 | Kallok et al. |
| 5,170,802 A | 12/1992 | Mehra |
| 5,265,604 A | 11/1993 | Vince |

(Continued)

FOREIGN PATENT DOCUMENTS

| | | |
|---|---|---|
| EP | 1588735 A1 | 10/2005 |
| WO | 2008092246 A1 | 8/2008 |

OTHER PUBLICATIONS

Canadian Office Action dated Jan. 4, 2016 for corresponding Canadian Application No. 2,865,410, filed Sep. 14, 2014.

(Continued)

*Primary Examiner* — Christopher Koharski
*Assistant Examiner* — Pamela M. Bays
(74) *Attorney, Agent, or Firm* — Westman, Champlin & Koehler, P.A.

(57) ABSTRACT

An implantable medical device for treating breathing disorders such as central sleep apnea wherein stimulation is provided to the phrenic never through a transvenous lead system with the stimulation beginning after inspiration to extend the duration of a breath and to hold the diaphragm in a contracted condition.

14 Claims, 8 Drawing Sheets

(56) References Cited

U.S. PATENT DOCUMENTS

| | | | |
|---|---|---|---|
| 5,483,969 A * | 1/1996 | Testerman | A61B 5/1135 600/529 |
| 5,485,851 A | 1/1996 | Erickson | |
| 6,006,134 A * | 12/1999 | Hill et al. | 607/9 |
| 6,132,384 A | 10/2000 | Christopherson et al. | |
| 6,212,435 B1 | 4/2001 | Lattner et al. | |
| 6,266,564 B1 | 7/2001 | Hlll et al. | |
| 6,360,740 B1 | 3/2002 | Ward et al. | |
| 6,415,183 B1 | 7/2002 | Scheiner et al. | |
| 6,449,507 B1 | 9/2002 | Hill et al. | |
| 6,463,327 B1 | 10/2002 | Lurie et al. | |
| 6,532,388 B1 | 3/2003 | Hill et al. | |
| 6,537,228 B1 | 3/2003 | Lambert | |
| 6,542,774 B2 | 4/2003 | Hill et al. | |
| 6,587,726 B2 | 7/2003 | Lurie et al. | |
| 6,589,188 B1 | 7/2003 | Street et al. | |
| 6,641,542 B2 | 11/2003 | Cho et al. | |
| 6,684,101 B2 | 1/2004 | Daum | |
| 6,718,208 B2 | 4/2004 | Hill et al. | |
| RE38,705 E | 2/2005 | Hill et al. | |
| 6,881,192 B1 | 4/2005 | Park | |
| 6,890,306 B2 | 5/2005 | Poezevera | |
| 6,928,324 B2 | 8/2005 | Park et al. | |
| 6,934,583 B2 | 8/2005 | Weinberg et al. | |
| 6,937,903 B2 | 8/2005 | Schuler et al. | |
| 6,964,641 B2 | 11/2005 | Cho et al. | |
| 7,025,730 B2 | 4/2006 | Cho et al. | |
| 7,070,568 B1 | 7/2006 | Koh | |
| 7,077,132 B2 | 7/2006 | Berthon-Jones | |
| 7,082,331 B1 * | 7/2006 | Park et al. | 607/42 |
| 7,094,207 B1 | 8/2006 | Koh | |
| 7,155,278 B2 | 12/2006 | King et al. | |
| 7,179,229 B1 | 2/2007 | Koh | |
| 7,184,829 B2 | 2/2007 | Hill et al. | |
| 7,200,442 B1 | 4/2007 | Koh et al. | |
| 7,212,862 B2 | 5/2007 | Park et al. | |
| 7,223,244 B1 | 5/2007 | Koh | |
| 7,225,019 B2 | 5/2007 | Jahns et al. | |
| 7,225,021 B1 | 5/2007 | Park et al. | |
| 7,245,971 B2 | 7/2007 | Park et al. | |
| 7,269,457 B2 | 9/2007 | Shafer et al. | |
| 7,269,459 B1 | 9/2007 | Koh | |
| 7,277,757 B2 | 10/2007 | Casavant et al. | |
| 7,340,302 B1 | 3/2008 | Falkenberg et al. | |
| 7,357,775 B1 | 4/2008 | Koh | |
| 7,361,146 B1 | 4/2008 | Bharmi et al. | |
| 7,363,086 B1 | 4/2008 | Koh et al. | |
| 7,371,220 B1 | 5/2008 | Koh et al. | |
| 2001/0003799 A1 | 6/2001 | Boveja | |
| 2003/0195571 A1 * | 10/2003 | Burnes et al. | 607/9 |
| 2005/0085734 A1 | 4/2005 | Tehrani | |
| 2005/0085865 A1 | 4/2005 | Tehrani | |
| 2005/0085866 A1 | 4/2005 | Tehrani | |
| 2005/0085867 A1 | 4/2005 | Tehrani et al. | |
| 2005/0085868 A1 * | 4/2005 | Tehrani et al. | 607/42 |
| 2005/0085869 A1 | 4/2005 | Tehrani et al. | |
| 2005/0165457 A1 * | 7/2005 | Benser et al. | 607/42 |
| 2005/0197588 A1 | 9/2005 | Freeberg | |
| 2005/0288729 A1 | 12/2005 | Libbus et al. | |
| 2006/0030894 A1 | 2/2006 | Tehrani et al. | |
| 2006/0036294 A1 | 2/2006 | Tehrani | |
| 2006/0122662 A1 * | 6/2006 | Tehrani et al. | 607/42 |
| 2006/0142815 A1 | 6/2006 | Tehrani et al. | |
| 2006/0149334 A1 | 7/2006 | Tehrani et al. | |
| 2006/0155341 A1 | 7/2006 | Tehrani et al. | |
| 2006/0167523 A1 | 7/2006 | Tehrani et al. | |
| 2006/0229677 A1 | 10/2006 | Moffitt et al. | |
| 2006/0247729 A1 | 11/2006 | Tehrani et al. | |
| 2007/0021795 A1 | 1/2007 | Tehrani | |
| 2008/0154330 A1 | 6/2008 | Tehrani et al. | |
| 2008/0161878 A1 | 7/2008 | Tehrani et al. | |
| 2008/0167695 A1 | 7/2008 | Tehrani et al. | |
| 2008/0177347 A1 | 7/2008 | Tehrani et al. | |
| 2008/0183239 A1 | 7/2008 | Tehrani et al. | |
| 2008/0183240 A1 | 7/2008 | Tehrani et al. | |
| 2008/0183264 A1 | 7/2008 | Bly et al. | |
| 2008/0188903 A1 | 8/2008 | Tehrani et al. | |
| 2008/0188904 A1 | 8/2008 | Tehrani et al. | |

OTHER PUBLICATIONS

Canadian Office Action dated Nov. 17, 2016 for corresponding Canadian Application No. 2,865,410.
International Search Report of International Application PCT/US2006/0447 (dated Aug. 15, 2007), 3 pp.
Written Opinion of the International Searching Authority of International application PCT/US2006/044788 (dated Apr. 12, 2007), 3 pp.
international Preliminary Report on Patentability of International Application PCT/US2006/044788 (dated May 20, 2008), 4 pp.
Redline, Susan et al., Beyond the Fat Boy, Journal of Applied Physiology 2005, vol. 99: pp. 1243-1244.
Esler, Murray et al., Is Obstructive Sleep Apnea the Cause of Sympathetic Nervous Activation in Human Obesity?, Journal of Applied Physiology 2006, vol. 100, pp. 11-12.
Caples, Sean M. et al., Influence of Cardiac Function and Failure on Sleep-Disordered Breathing, Journal of Applied Physiology 2005, vol. 99, pp. 2433-2439.
Punjabi, Naresh M. et al., Disorders of Glucose Metabolism in Sleep Apnea, Journal of Applied Physiology 2005, vol. 99, pp. 1998-2007.
Leuenberger, Urs A. et al., Hypoxia Augments Apnea-Induced Peripheral Vasoconstriction in Humans, Journal of Applied Physiology 2001, vol. 95, pp. 2023-2029.
Oliven, Arie, et al., Upper Airway Response to Electrical Stimulation of the Genioglossus in Obstructive Sleep Apnea, Journal of Applied Physiology 2003, vol. 95, pp. 2023-2029.
Parati, Gianfranco et al., Sleep Apnea: Epidemiology, Pathophysiology, and Relation to Cardiovascular Risk, Am Journal Physiological Society 2007, vol. 293, pp. R1671-R1683.
Gottfried, Stewart B. et al., Effects of Phrenic Stimulation on Upper Airway Resistance in Anethetized Dogs, Am Physiological Society 1983, 0161-7567/83, pp. 419-426.
Planas, Roque F. et al., Diaphragmatic Pressures: Transvenous vs. Direct Phrenic Nerve Stimulation, Am Physiological Society 1985, 0161-7567/85, pp. 269-273.
Series, F. et al., Site of Phrenic Nerve Stimulation-Induced Upper Airway Collapse: Influence of Expiratory Time, Journal of Applied Physiology 2002, vol. 92, pp. 665-671.
Kingma, John G. Jr. et al., Neuromodulation Therapy Does Not Influence Blood Flow Distribution or Left-Ventricular Dynamics During Acute Myocardial Ischemia, Autonomic Neuroscience: Basic and Clinical 91 (2001) pp. 47-54.
Linderoth, Bengt, MD, PHD et al., Mechanisms of Spinal Cord Stimulation in Painful Syndromes: Role of Animal Models, American Academy of Pain Medicine, vol. 7, No. S14-S26, 2006.
Tanaka, Satoshi et al., Mechanisms of Sustained Cutaneous Vasodilation Induced by Spinal Cord Stimulation, Autonomic Neuroscience: Basic and Clinical 114 (2004) pp. 55-60.
Lorenzi-Filho, Geraldo et al., Cheyne-Stokes Respiration in Patients with Congestive Heart Failure: Causes and Consequences, Clinics 2005; 60(4):333-44.
Brack, Thomas, Cheyne-Stokes Respiration in Patients with Congestive Heart Failure, Swiss Med Wkly 2003; 133:605-610, www.smw.ch.
Yumino, Dai et al., Central Sleep Apnea and Cheyne-Stokes Respiration, Proceedings of the American Thoracic Society, 2008, vol. 5, pp. 226-236.
Garrido-Garcia, H. et al., Treatment of Chronic Ventilatory Failure Using a Diaphragmatic Pacemaker, Spinal Cord (1998) 36, 310-314.
Diedrichs, Holger et al., Symptomatic Relief Precedes Improvement of Myocardial Blood Flow in Patients Under Spinal Cord Stimulation, BioMed Central, 2005, pp. 1-7.
Kaneko, S. et al., A New Approach to Respiratory Assist for Phrenic Nerve Paralysis, Trans Am Soc. Artif Intern Organs, 1985, vol. XXXI, pp. 301-304.

(56) References Cited

OTHER PUBLICATIONS

Macintyre, Neil R., MD, Setting the Frequency-Tidal Volume Pattern, www.rcjournal.com/contents/03.02/03.02.0266.asp.
Kohnlein, T. et al., Central Sleep Apnea Syndrome in Patients with Chronic Heart Disease: A Critical Review of the Current Literature, Thorax 2002; 57:547-554.
Javaheri, Shahrokh, MD, Central Sleep Apnea in Congestive Heart Failure: Prevalence, Mechanisms, Impact, and Therapeutic Options, Seminars in Respiratory and Critical Care Medicine, 2005, vol. 26, No. 1.
Dobelle, William H., Use of Breathing Pacemakers to Suppress Intractable Hiccups of up to Thirteen Years Duration, ASAIO Journal 1999, pp. 524-525.
Series, Frederic, Assessment of Upper Airway Dynamics in Awake Patients with Sleep Apnea Using Phrenic Nerve Stimulation, Am Journal Respir Crit Care Med, 2000, vol. 162., pp. 795-800.
Bilgutay, A.M. et al., Augmented Ventilation by Synchronous Phrenic Nerve Stimulation, Trans. Amer. Soc. Artif. Int. Organs, 1970, vol. XVI, pp. 213-217.
Yasuma, Fumihiko et al., Eight-Year Follow-Up Study of a Patient with Central Alveolar Hypoventilation Treated with Diaphragm Pacing, Respiration, 1998; 65:313-316.
Handa, Y. et al., Basic Strudies on Electrophrenic Respiration Part 2—Assisted Ventilation by the Synchronous Electrophrenic Respirator, Medical and Biological Engineering, Jul. 1976.
Kimura, M. et al., A Heart-Rate-Responsive Diaphragm Pacemaker, Med. & Biol. Eng. & Comput., 1987, 25, 458-462.
Kimura, M. et al., Heart Rate and Body Temperature Sensitive Diaphragm Pacing, Med. & Biol. Eng. & Comput. 1992, 30, 155-161.
Kimura, M. et al., Addition to an RF-Coupled Phrenic Nerve Stimulator Implant to Provide Outward Transmission of Body Temperature, Med. & Biol. Eng. & Comput. 1986, 24, 659-661.
Taira, Takaomi, MD, Ph.D et al., Phrenic Nerve Stimulation for Diaphragm Pacing with a Spinal Cord Stimulator, Elsevier Science, Surg Neurol, 2003; 59:128-32.
Chatfield, Paul O. et al., Role of Pulmonary Proprioceptive Reflexes in Suppression of Spontaneous Breathing During Electrophrenic Respiration, Dept. of Physiology, Harvard Medical School, and Dept. of Physiology, Harvard School of Public Health, vol. 163.
Sarnoff, Stanley J. et al., Electrophrenic Respiration. III. Mechanism of the Inhibition of Spontaneous Respiration, Dept. of Physiology, Harvard School of Public Health, 1948, vol. 155, pp. 203-207.
Sarnoff, Stanley J. et al., Electrophrenic Respiration IV. The Effectiveness of Contralateral Ventilation During Activity of One Phrenic Nerve, Dept. of Physiology, Harvard School of Public Health, 1949, pp. 929-937.
Stemmer, Edward A. MD et al., Dioaphragmatic Pacing in the Treatment of Hypoventilation Syndrome, Journal of Thoracic and Cardiovascular Surgery, vol. 54, No. 5, 1967, pp. 649-657.
Furman, Seymour, MD et al., Transvenous Stimulation of the Phrenic Nerves, Journal of Thoracic and Cardiovascular Surgery, vol. 62, No. 5, 1971, pp. 743-751.
Aiyar, Harish et al., Diaphragm Pacing for Chronic Respiratory Insufficient, CRC Press, LLC, 2001, Chapter 9.
Canadian Office Action dated Jun. 29, 2018 for corresponding Canadian Application No. 2,865,410, filed Sep. 26, 2014.
Canadian Office Action dated Jul. 12, 2017 for corresponding Canadian Application No. 2,865,410, filed Sep. 26, 2014.
Canadian Office Action for CA 2,865,410, dated May 3, 2019, 4 Pages.

* cited by examiner

SYSTEM AND METHOD TO MODULATE PHRENIC NERVE TO PREVENT SLEEP APNEA

CROSS-REFERENCE TO RELATED CASES

This application is a continuation of U.S. patent application Ser. No. 11/601,150 filed Nov. 17, 2006, now U.S. Pat. No. 8,244,359, entitled: "System and Method to Modulate Phrenic Nerve to Prevent Sleep Apnea," and claims priority from and the benefit thereof and incorporates: U.S. Provisional Application 60/737,808, filed Nov. 18, 2005, and entitled "System and Method to Modulate Phrenic Nerve to Prevent Sleep Apnea;" U.S. Provisional Application 60/743,062, filed Dec. 21, 2005, and entitled "System and Method to Modulate Phrenic Nerve to Prevent Sleep Apnea;" and U.S. Provisional Application 60/743,326, filed Feb. 21, 2006, and entitled "System and Method to Modulate Phrenic Nerve to Prevent Sleep Apnea."

FIELD OF THE INVENTION

The present invention relates generally to implantable medical devices and more particularly to a device and method for controlling breathing and for treating Central Sleep Apnea.

BACKGROUND OF THE INVENTION

History

Sleep Disordered Breathing (SDB) and particularly Central Sleep Apnea (CSA) is a breathing disorder closely associated with Congestive Heart Failure (CHF). The heart function of patients with heart failure may be treated with various drugs, or implanted cardiac pacemaker devices. The breathing function of patients with heart failure may be treated with Continuous Positive Air Pressure (CPAP) devices or Nocturnal Nasal Oxygen. These respiratory therapies are especially useful during periods of rest or sleep. Recently, implanted devices to directly address respiration disturbances have been proposed. Some proposed therapeutic devices combine cardiac pacing therapies with phrenic nerve stimulation to control breathing.

Phrenic nerve pacing as a separate and stand alone therapy has been explored for paralyzed patients where it is an alternative to forced mechanical ventilation, and for patients with the most severe cases of central sleep apnea. For example, Ondine's Curse has been treated with phrenic nerve pacemakers since at least the 1970's. In either instance, typically, such phrenic nerve pacemakers place an electrode in contact with the phrenic nerve and they pace the patient's phrenic nerve at a constant rate. Such therapy does not permit natural breathing and it occurs without regard to neural respiratory drive.

Motivation for Therapy

SDB exists in two primary forms. The first is central sleep apnea (CSA) and the second is obstructive sleep apnea (OSA). In OSA the patient's neural breathing drive remains intact, but the pulmonary airways collapse during inspiration, which prevents air flow causing a form of apnea. Typically, such patients awake or are aroused as a result of the apnea event. The forced airflow of CPAP helps keep the airways open providing a useful therapy to the OSA patient.

CSA patients also exhibit apnea but from a different cause. These CSA patients have episodes of reduced neural breathing drive for several seconds before breathing drive returns. The loss of respiratory drive and apnea is due to a dysfunction in the patient's central respiratory control located in the brain. This dysfunction causes the patient's breathing pattern to oscillate between too rapid breathing called hyperventilation and periods of apnea (not breathing). Repeated bouts of rapid breathing followed by apnea are seen clinically and this form of disordered breathing is called Cheyne-Stokes breathing or CSR. Other patterns have been seen clinically as well including bouts of hyperventilation followed by hypopneas only.

In patients with CHF, prognosis is significantly worse when sleep apnea is present A high apnea-hypopnea index (a measure of the number of breathing disturbances per hour) has been found to correlate to a poor prognosis for the patient. The swings between hyperventilation and apnea characterized by central sleep apnea have three main adverse consequences, namely: large swings in arterial blood gases (oxygen and carbon dioxide); arousals and shifts to light sleep; and large negative swings in intrathoracic pressure during hyperventilation. The large swings in blood gases lead to decreased oxygen flow to the heart, activation of the sympathetic nervous system, endothelial cell dysfunction, and pulmonary arteriolar vasoconstriction. Arousals contribute to increased sympathetic nervous activity, which has been shown to predict poor survival of patients with heart failure. Negative intrathoracic pressure, which occurs during the hyperventilation phase of central apnea, increases the after load and oxygen consumption of the left ventricle of the heart. It also causes more fluid to be retained in the patient's lungs. As a result of these effects the patient's condition deteriorates.

In spite of advances in care and in knowledge there is a large unmet clinical need for patients with sleep disordered breathing especially those exhibiting central sleep apnea and congestive heart failure.

SUMMARY OF THE INVENTION

The device of the present invention can sense the patients breathing and it can distinguish inhalation or inspiration from exhalation or expiration.

The device can periodically stimulate the phrenic nerve as required. In some embodiments the stimulation may be invoked automatically in response to sensed physiologic conditions. In some embodiments the device can stop the delivery of therapy in response to sensed conditions. In some embodiments the device can be prescribed and dispensed and the therapy delivered without regard to the sensed conditions. As a result, the device may be used to detect and intervene in order to correct episodes of sleep disordered breathing or the device may intervene to prevent episodes of sleep disordered breathing from occurring. The methods that are taught here may be used alone to treat a patient or they may be incorporated into a cardiac stimulating device where the respiration therapy is merged with a cardiac therapy. The therapy and its integration with cardiac stimulation therapy and the architecture for carrying out the therapy are quite flexible and may be implemented in any of several forms.

Hardware implementation and partitioning for carrying out the methods of the invention are also flexible. For example the phrenic nerve stimulation may be carried out with a transvenous lead system lodged in one of the cardiophrenic vein a short distance from the heart. One or both phrenic nerves may be accessed with leads. Either one side or both (right and left) phrenic nerves may be stimulated. Alternatively the phrenic nerve may be accessed through a large vein such as the jugular or the superior vena cava.

Because of the variety of anatomy and branching of the smaller veins, all non-central veins proximate to the phrenic nerve, including the pericardiophrenic, are call "phrenic nerve". For example, the left or right pericadiophrenic veins are suitable for left or right phrenic nerve stimulation because of their proximity to the phrenic nerves, relatively simple catheter access, relative distance and separation from the excitable heart tissue by non-excitable tissue such as the pericardial membrane. Preferred placement of a stimulation electrode can be characterized by: not triggering heartbeat when stimulation current is applied, trigging breath, minimum phrenic nerve stimulation current, and lack of stimulation of different muscle groups not involved in respiration. As an alternative, a stimulation electrode may be placed in the pericardial space on the heart, near the phrenic nerve but electrically isolated from the heart.

The lead and stimulation electrodes may also take any of several forms. Leads may contain anchoring devices to prevent slippage. Multiple stimulation electrodes may be placed along the length of a lead. Any pair of these electrodes may be used for bipolar stimulation. The stimulator may switch between different electrodes to achieve capture of the phrenic nerve at a minimum energy level without stimulating the heart. Any electrode may be used as a sensory electrode, even those engaged in intermittent stimulation. Monopolar stimulation may also be used. When the electrode is monopolar, the reference electrode is likely the stimulator case. Leads may be coated with medications such as, but not limited to, steroids.

Implementation of respiration detection and measurement may also take any of several forms. Transthoracic impedance measurement may be taken from electrodes implanted at locations in the body to measure or sense the change in lung volume associated with breathing. Alternatively one or more implanted pressure transducers in or near the pleural cavity may be used to track pressure changes associated with breathing. Alternatively, respiration sensing may be carried out by an airflow sensor, a respiratory belt, a temperature sensor, a humidity sensor, and/or a CO2 sensor. In conjunction, or in alternative, sensing electrodes may be used to sense events such as cardiac electrical activity, patient activity, patient metabolic state. Knowledge of breathing rates and patterns are useful in carrying out the invention but distinguishing reliably the inspiration phase from expiration phase is a breath is particularly important for timing the delivery of the stimulation.

Any detection system used to trigger stimulation has a disadvantage of being susceptible to non-respiratory signals such as an artifact of motion, sudden arousal, or cough. The recognition of possible artifacts and comparison to stored breath history of normal breath patterns may be advantageous. If a given breathing pattern significantly differs from the template, then the breath may be rejected and stimulation deferred. Artifacts may be recognized and rejected by identification of: an unacceptably fast inhalation slope, an unacceptably high amplitude of tidal volume and/or the presence of a high frequency component in the respiratory signal spectrum. In all cases the stimulator logic may reject this "breath" and not apply a stimulation burst. It may also be useful to reject signals for some duration immediately following a stimulation pulse. This so-called "refractory period" may be measured as the duration of stimulation plus minimum time of expiration. In addition, an implantable stimulator may be equipped with an accelerometer. Acceleration signals may be used to reject a breath or several breaths and delay stimulation. After a normal pattern of breathing is restored, stimulation is resumed.

We consider that breathing has an inspiration phase followed by an expiration phase. Each breath is followed by a pause when the lungs are "still" before the next breath's inspiration. The device delivers phrenic nerve stimulation after the start of inspiration preferably toward the start of exhalation. The duration and magnitude of the stimulation is selected to "extend" the expiration phase or the respiratory pause of a naturally initiated breath. We note relatively little change in lung volume and little air exchange during the stimulation phase of the therapy. We have observed that prolongation of a natural breath, while keeping some air trapped in the lungs, delays the inspiration phase of next natural breath until the air trapped in the lungs is exhaled. For this reason our therapy has a tendency to lower the observed breathing rate. Typically the stimulation maintains activation of the diaphragm long enough to mimic a patient holding their breath by not letting the diaphragm relax. This mechanism of action controls the rate of breathing by increasing the effective duration of each breath.

Our experimental animal work has demonstrated the ability of the stimulation regime to down-regulate breathing rate (and minute ventilation) to a desired (preset) value while maintaining natural inspiration (i.e. by prolonging exhalation and extending the respiratory pause phases of the breath) without blocking the phrenic nerve. We believe that maintenance of natural inspiration is important since it allows prevention of airway collapse and retains certain capacity of the body to auto regulate rate of inspiration and depth of breathing. We also demonstrated that unilateral and transvenous stimulation is sufficient to carry out the invention and insures adequate levels of patient safety. In the process of prolonging the respiratory pause we "stilled" the lungs (no air movement occurred) while keeping one lung inflated. We believe that the mechanism of action for this observed effect is a physiologic feedback that prevents the respiration control center of the central nervous system from initiating the following breath. In other words we have invented a novel and practical therapy by substantially immobilizing at least one lung of the patient by maintaining the diaphragm in the contracted state by transvenous electrical stimulation of a phrenic nerve for the duration sufficient to substantially reduce breathing rate and alter the blood gas composition of the patient.

BRIEF DESCRIPTION OF THE DRAWINGS

A preferred embodiment and best mode of the invention is illustrated in the attached drawings where identical reference numerals indicate identical structure throughout the figures and where multiple instances of a reference numeral in a figure show the identical structure at another location to improve the clarity of the figures, and where.

DETAILED DESCRIPTION OF THE INVENTION

Figure 1:
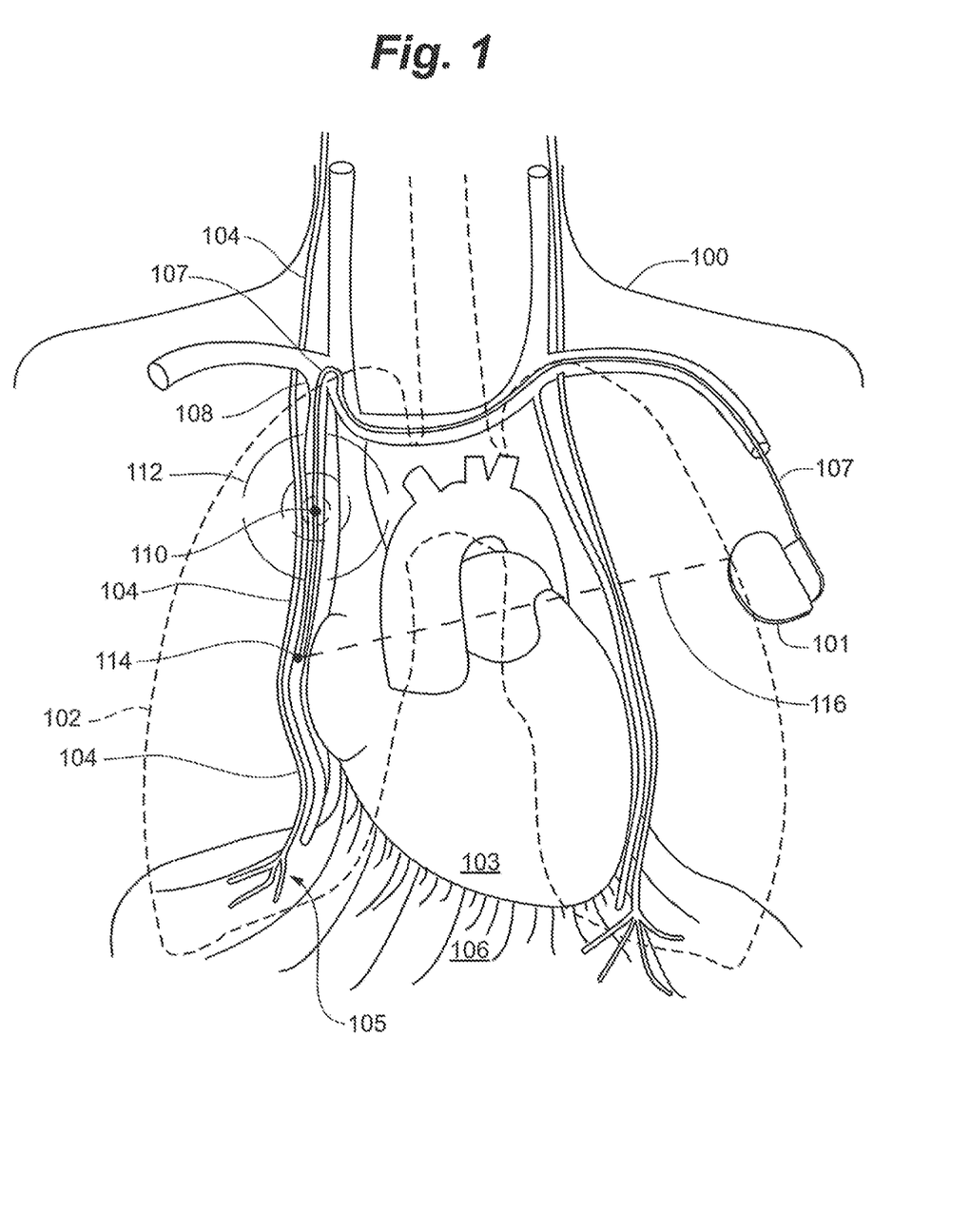
FIG. 1 is a schematic diagram.

FIG. 1 is schematic diagram showing an implanted medical device (IMD) 101 implanted in a patient's chest for carrying out a therapeutic stimulation of respiration. The patient has lungs shown in bold outline and indicated at 102 overlying the heart 103. The right phrenic nerve 104 passes from the head alongside the heart to innervate the diaphragm 106 at location 105.

In this embodiment a transvenous lead 107 passes from the IMD 101 and passes through venous vasculature to enter the cardiophrenic vein 108 on the right side of the patient. The cardiophrenic vein 108 lies next to the phrenic nerve 104 along the heart. Electrical stimulation pulses supplied to the stimulation electrode 110 on lead 107 interact with the phrenic nerve to stimulate it and thus activate the diaphragm 106. In the figure a series of concentric circles 112 indicate electrical stimulation of the phrenic nerve. In this embodiment the stimulation electrode 110 lies far enough away from the heart 103 to avoid stimulating the heart 103. In this embodiment only one branch of the phrenic nerve 104 is stimulated and the other side of nerve is under normal physiologic control.

A respiration electrode 114 on lead 107 cooperates with an indifferent electrode on the can of the IMO 101 to source and sink low amplitude electrical pulses that are used to track changes in lung volume over time. This well known impedance plethysmography technique is used to derive the inspiration and expiration events of an individual breath and may be used to track breathing rate, This impedance measurement process is indicated in the diagram by the dotted line 116 radiating from the electrode site of respiration electrode 114 to the IMD 101. Transvenous stimulation of the phrenic nerve from a single lead carrying an impedance measuring respiration electrode is a useful system since it permits minimally invasive implantation of the system. However other architectures, are permissible and desirable in some instances.

Figure 2:
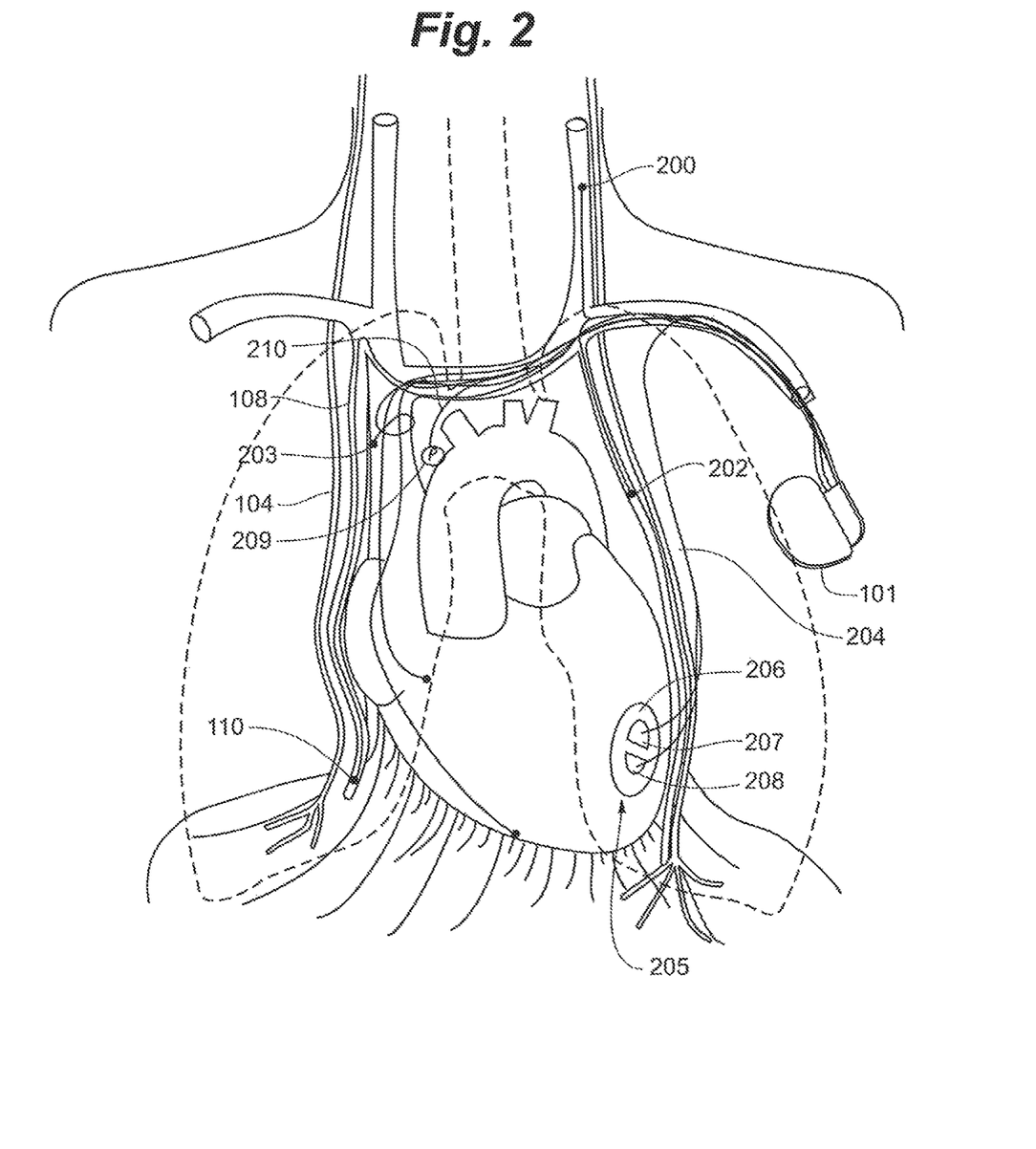
FIG. 2 is a schematic diagram.

FIG. 2 is a schematic diagram showing alternative electrode and lead placements for use in carrying out the stimulation regime of the invention. In some patients it may be easier or more suitable to access the phrenic nerve in the neck in the jugular vein at electrode location 200. In some instances it may be preferable to place electrodes in veins both near the right phrenic nerve as indicated by the deep location of a stimulation electrode 110 and in the left phrenic nerve at electrode location 202. Other potential locations for the stimulation electrodes are the large vessel (SVC) above the heart indicated by electrode 203. Unilateral stimulation is preferred but having multiple sites available may be used to reduce nerve fatigue. Non-venous placement is possible as well. For example, placement of a patch electrode in the pericardial space between the heart and within the pericardial sac is suitable as well, as indicated by electrode location 205. In this embodiment the insulating patch 206 isolates spaced electrodes 207 and electrode 208 from the heart. The lead 204 connects this bipolar pair of electrodes to the IMD 101.

Also seen in this figure is a pressure transducer 209 located in the pleural cavity and connected to the IMD 101 via a lead. The pressure transducer 209 tracks pressure changes associated with breathing and provides this data to the implanted device 101. The pressure transducer is an alternative to the impedance measurement system for detecting respiration. Such intraplueral pressure signal transducers are known in the respiration monitoring field.

Figure 3:
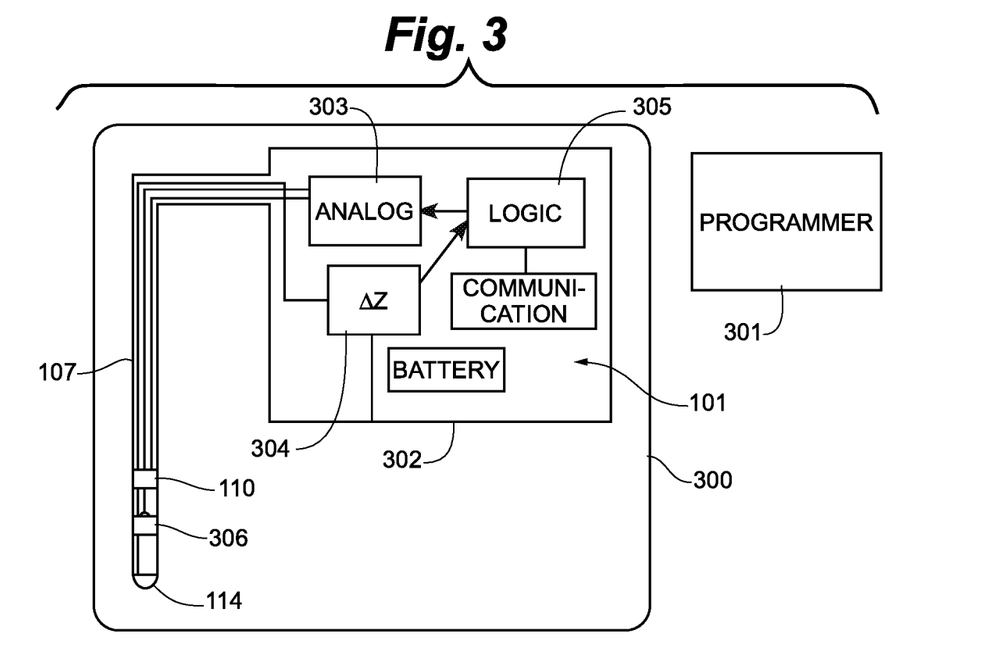
FIG. 3 is a schematic diagram.

FIG. 3 shows a schematic diagram of a system for carrying out the invention. The system has an implanted portion 300 and an external programmer portion 301.

The IMD 101 can provide stimulation pulses to the stimulation electrode 110. A companion indifferent electrode 306 may be used to sink or source the stimulation current generated in analog circuits 303. A portion of the exterior surface 302 of the IMD 101 may be used with respiration electrode 114 to form an impedance plethysmograph. In operation, logic 305 will command the issuance of a train of pulses to the respiration electrode 114 and measure the amplitude of the signal as a function of time in circuits 304. This well known process can measure the respiration of the patient and find the inspiration phase and the expiration phase of a breath. Respiration data collected over minutes and hours can be logged, transmitted, and/or used to direct the therapy.

When the therapy is invoked by being turned on by the programmer 301 or in response to high rate breathing above an intervention set point, the logic 305 commands the stimulation the phrenic nerve via the stimulation electrode 110 at a time after the beginning of the inspiration phase. Preferable the stimulation begins after the onset of exhalation. There is some flexibility in onset of stimulation. The shape of the stimulation pulses is under study and it may be beneficial to have the logic 305 command stimulation at higher amplitudes of energy levels as the stimulation progresses. It may also be desirable to have stimulation ramp up and ramp down during the therapy. It may prove desirable to stimulate episodically. The therapy may be best administered to .every other breath or in a random pattern. The programmer may permit the patient to regulate the therapy as well. However in each case the stimulation of the diaphragm "stills" the diaphragm resulting in an amount of air trapped in at least one lung and extends the breath duration.

The duration of the stimulation is under the control of logic 305. It is expected that the therapy will be dispensed with a fixed duration of pulses corresponding to breathing rate. It should be clear that other strategies for setting the duration of stimulation are within the scope of the invention. For example the breathing rate data can be used to set the stimulation duration to reduce breathing rate to a fraction of the observed rate. The therapy may also be invoked in response to detected high rate breathing or turned on at a fixed time of day. In a device where activity sensors are available the device may deliver therapy at times of relative inactivity (resting or sleeping). Activity sensors may also help in the detection and rejection of artifacts. An accelerometer, such as those used in cardiac pacing, would be an exemplary activity sensor.

Figure 4:
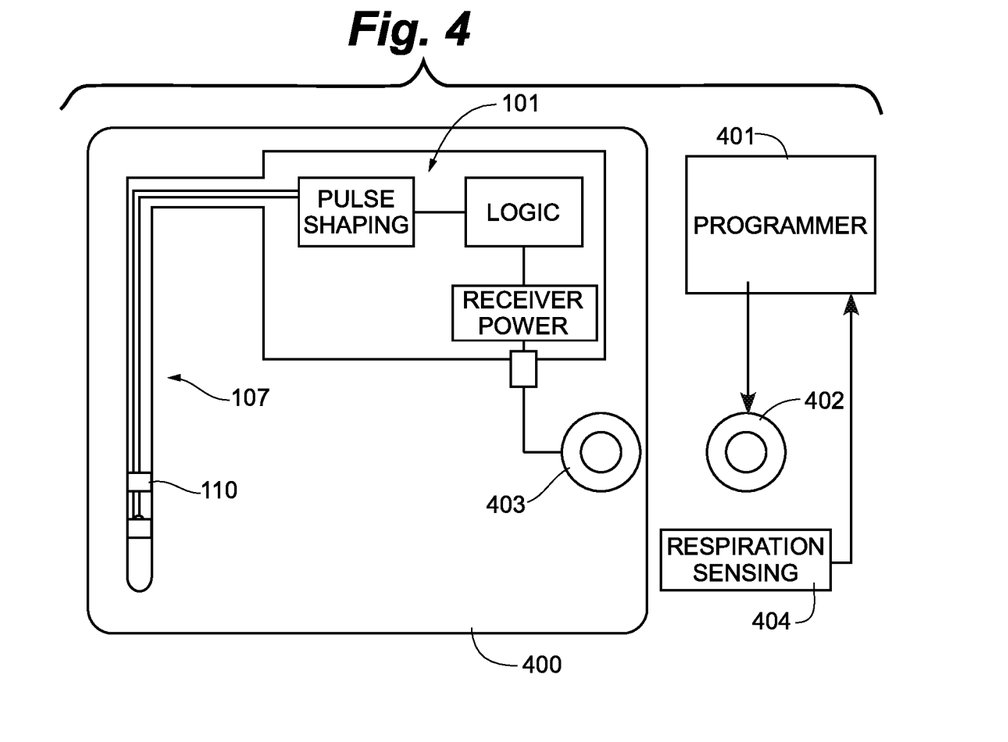
FIG. 4 is a schematic diagram.

FIG. 4 shows a schematic diagram of an alternate partitioning of the system. In this implementation, the respiration sensing is carried out outside the patient with sensor 404, while the implanted portion 400 communicates in real time with an external controller 401 via coils 403 and 402. This respiration sensor 404 may be a conventional respiration belt or thermistor based system. Real time breathing data is parsed in the controller 401 and control signal sent to the IPG 101 to drive stimulation of the phrenic nerve via lead 107. This implementation simplifies DAD 101 portion for the system and may be useful for delivery of therapy to a resting or sleeping patient.

Figure 5A:
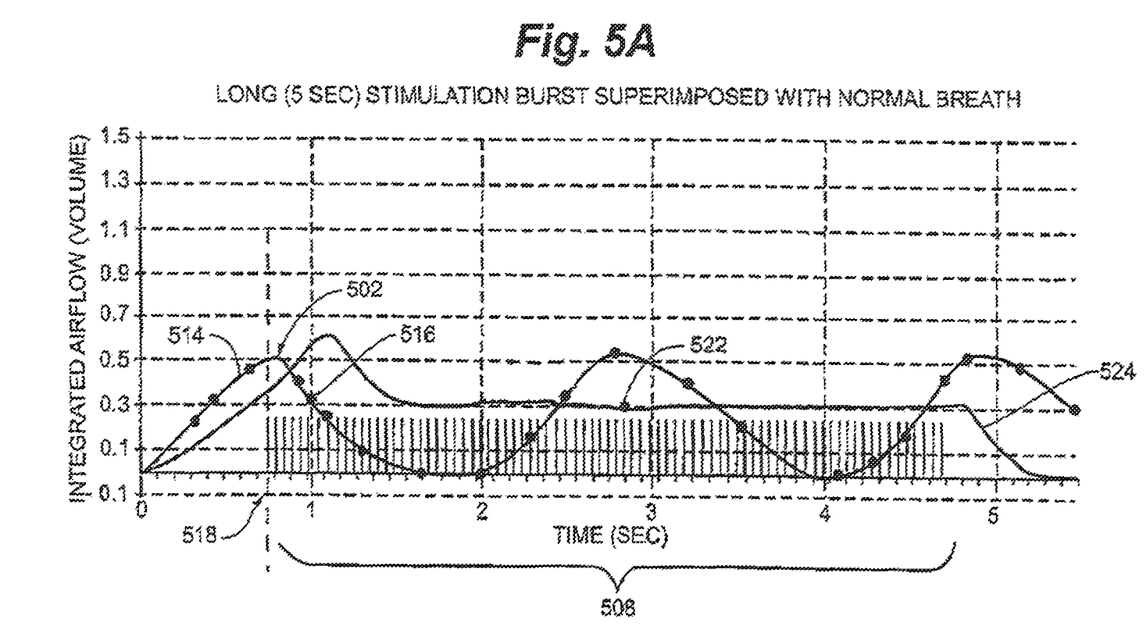
FIG. 5 is diagram showing experimentally derived physiologic data displayed in two panels A and B.
Figure 5B:
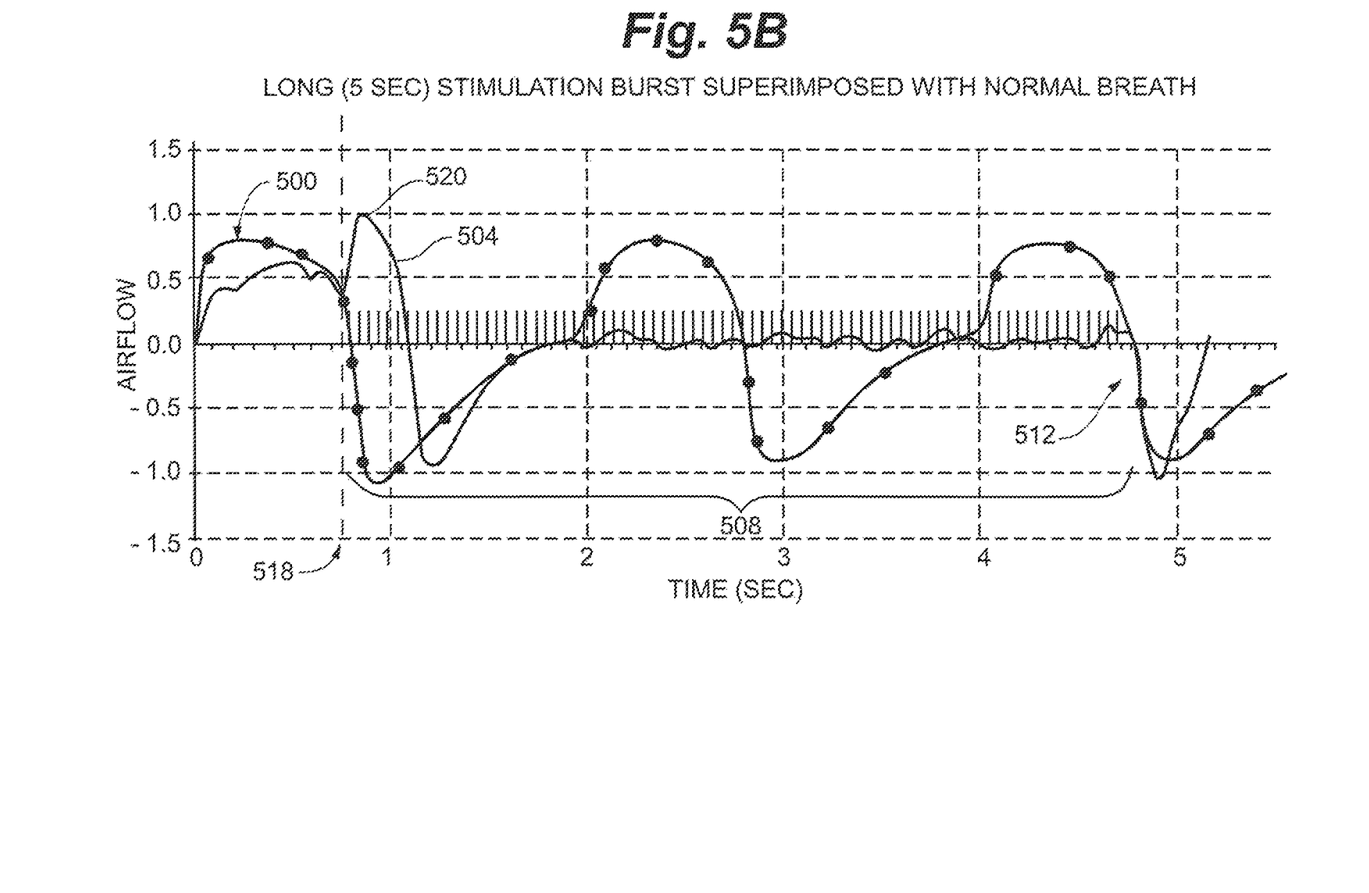

FIG. 5 is set forth as two panels. The data collected from an experimental animal (pig) is presented in the two panels and should be considered together. Panel 5B plots airflow into and out of the animal against time, while panel 5A plots volume against time. In the experiment the volume data was computed (integrated) from the airflow measurement. The two panels are two ways of looking at the same data collected at the same time. In each panel the dotted tracing 500 in 5B and 502 in panel 5A represent the normal or natural or not-stimulated and therefore underlying breathing pattern of the animal. In panel 5A the inspiration phase of tracing 502 is seen as segment 514. After tracing 502 peaks, the expiration phase begins as indicated by segment 516. The figure shows that along trace 502, the air that is inhaled is exhaled before 2 seconds has elapsed, as indicated by the dotted trace 502 returning to the zero volume level.

Trace 504 is associated with the unilateral delivery of stimulation 508 to a phrenic nerve. In the tracing the start of stimulation at time 518 is well after the start of inspiration and corresponds approximately to the reversal of airflow from inspiration to expiration as seen at time 518. Very shortly after the stimulation begins the animal inhales more air seen. by the "bump" 520 in the tracing 504 in pariel 5B. A small increment in the total volume corresponding to this bump is seen at the same time in panel 5A. Of particular interest is the relatively flat tracing 522 corresponding to no significant change in lung volume during stimulation. Once stimulation terminates the lungs expel air as seen at volume change 524 in panel 5A corresponding to outflow labeled 512 in panel 5B. Only after the exhalation outflow 512 was complete did the sedated experimental animal initiate the next breath (not shown). Thus duration of breath was extended in this case from approximately 2 seconds to approximately 6 seconds resulting in the breathing rate reduction from 30 to 10 breathe per minute. The data support the assertion that adequate phrenic stimulation initiated after inspiration and during expiration can "prolong" or "hold" the breath and thus regulate or regularize breathing which it the value of the invention.

Figure 6:
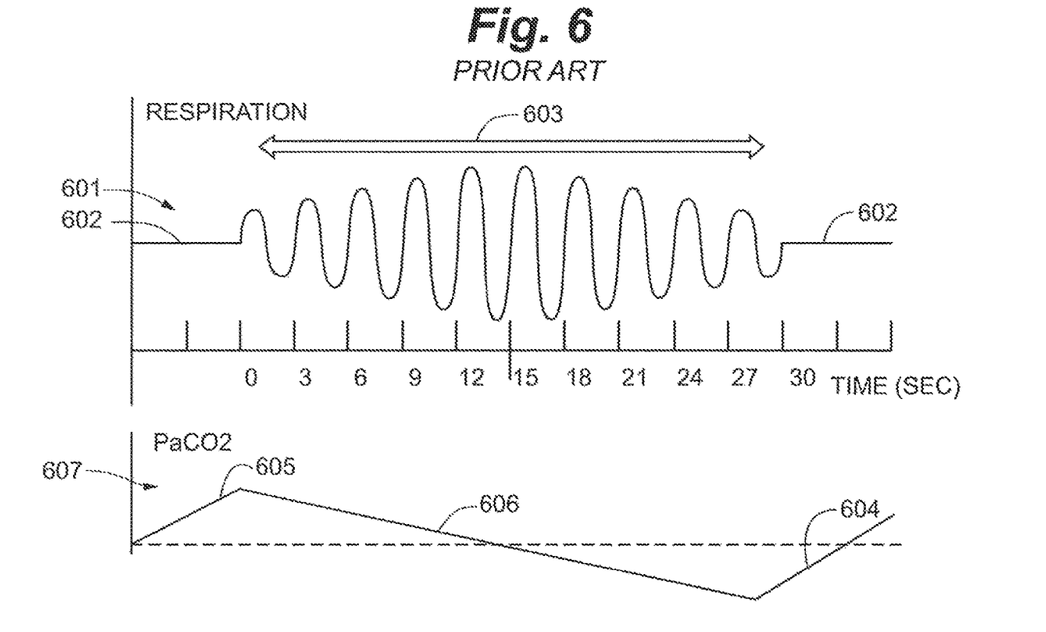
FIG. 6 is a schematic diagram showing physiologic data known in the prior art.

FIG. 6 shows a bout 601 of rapid breathing 603 followed by or preceded by apnea 602 events. This waveform is a presentation of Cheyne-Stokes respiration (CSR) well known in the prior art. The corresponding tracing of blood gas 607 indicates that the rapid breathing drives off blood carbon dioxide ($CO_2$) as indicated the slope of line 606. CSR begins with the rise of $CO_2$ as indicated by ramp line 605 which triggers the rapid breathing. The ventilation drives the $CO_2$ too low resulting in a loss of respiratory drive and an apnea event 602. During the apnea the level of $CO_2$ rises as indicated by the slope of line 604. Once a threshold is reached the cycle repeats.

Figure 7:
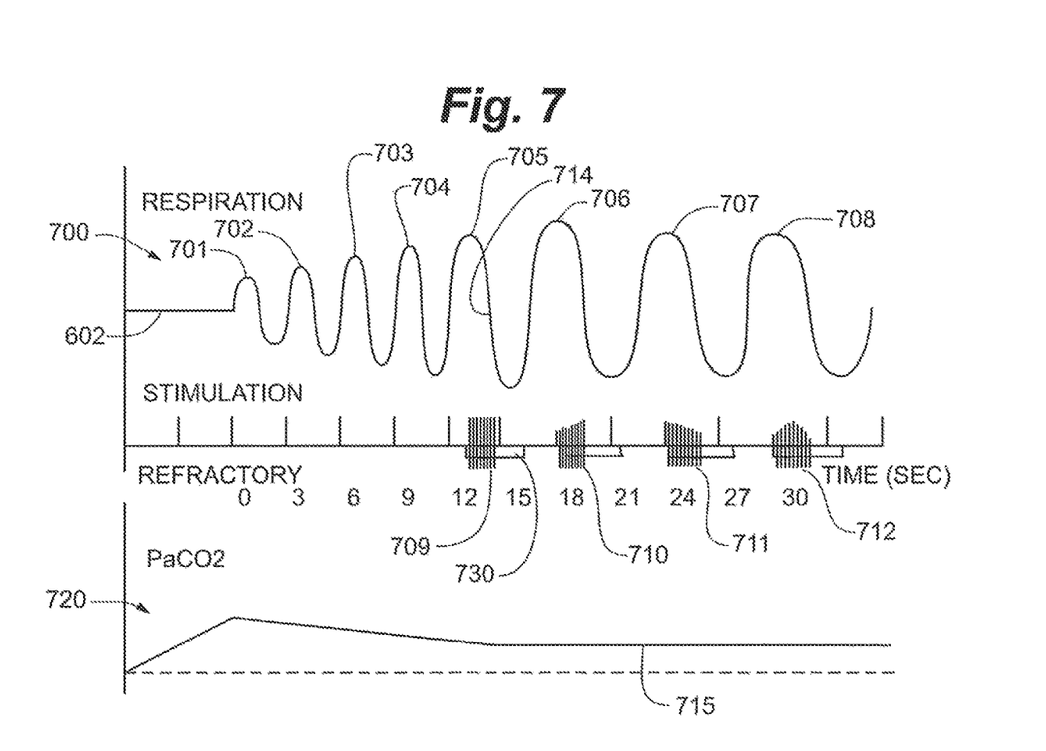
FIG. 7 is a schematic diagram showing physiologic data and device timing information.

FIG. 7 shows a schematic diagram showing the delivery of the inventive therapy in the context of a patient experiencing CSR respiration. The patient experiences several quick breaths 701 and then the device is turned on as indicated by the stimulation pulses 709. The device looks for a natural inspiration and waits until about the turn from inspiration to expiration, then the burst 709 of stimulation is delivered to a phrenic nerve. As explained in connection with FIG. 5 the stimulation delays breath 706. This next breath is also a candidate for the therapy and stimulation burst 710 is delivered to the phrenic nerve delaying breath 707. In a similar fashion the device intervenes in breaths 707 and 708. It is expected that the lower rate breathing resulting from repeated application of the therapy will keep the $CO_2$ level in a "normal" range 715 and prevent CSR. The therapy could also be invoked in response to a detected bout of CSR but this is not necessary and it is believed that keeping a patient out of CSR is the better therapy.

It may be noted that the stimulation waveforms vary in FIG. 7 with stimulation 710 rising in amplitude while stimulation 711 decreases in amplitude. Note as well that stimulation 712 ramps up and then down during the therapy. It is expected that the best waveform may vary from patient to patient or may vary over time. Also seen in the figure is a refractory period typified by period 730 that maybe implemented in the logic 302 to prevent the device from issuing the therapy too close in time to the last intervention. In general the refractory period effectively disables the deliver of therapy until the refractory period expires. This places an effective low rate on stimulated rate of breathing. The refractory may be fixed, programmable or adjusted based on sensed breathing rate.

Figure 8:
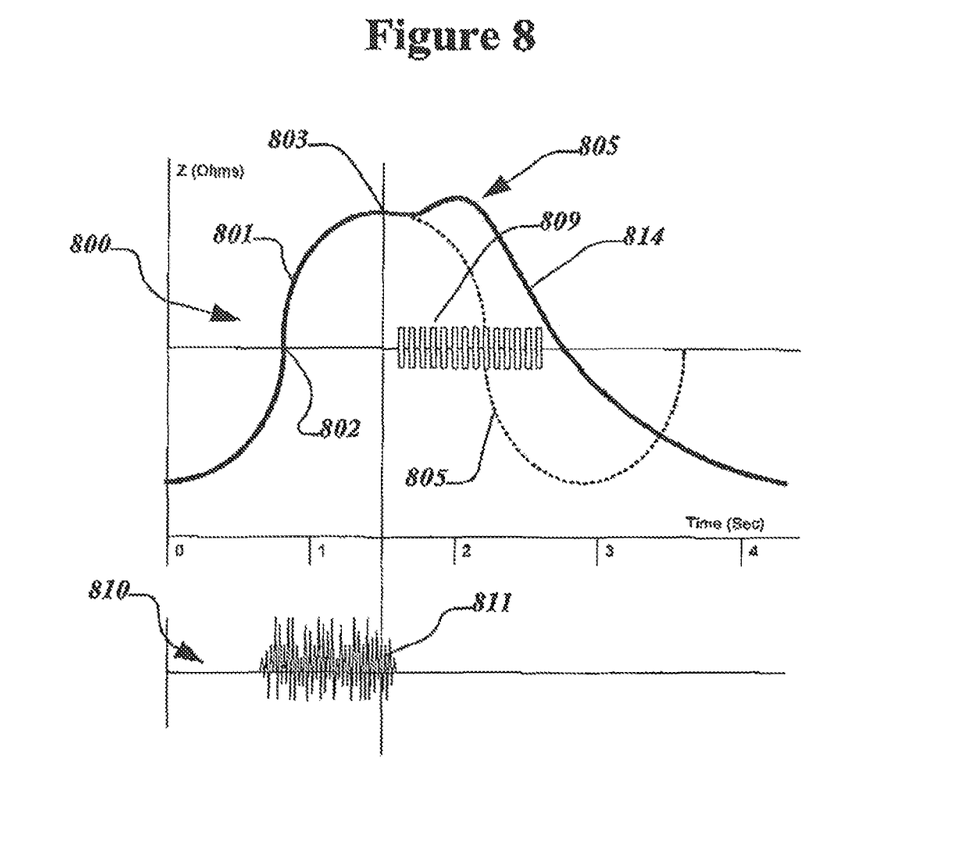
FIG. 8 is a schematic diagram showing physiologic data and device timing information.

FIG. 8 illustrates the concept of expiratory period stimulation to expand a native breath. Panel 800 shows the inspiratory period 801 of the native breath 805, the peak native inspiration 803 and the extended expiratory period 814. For comparison, trace 805 shows the expiration period of the same breath without stimulation. Panel 810 shows the native phrenic nerve excitation burst 811 that causes spontaneous inspiration 801. Without additional stimulation, inspiration would be over, and expiration will begin shortly after the duration of the native excitation burst. The phrenic nerve electrode stimulation burst 809 begins approximately at the time with the natural excitation 811 stops. This time point also approximately coincides with the peak native inspiration 803. The respiratory signal on panel 800 can be a transthoracic impedance signal. Point 802 marks the inspiratory turn. Preferably, stimulation may begin after a delay following the inspiratory turn point or after the peak inspiratory point.

Figure 9:
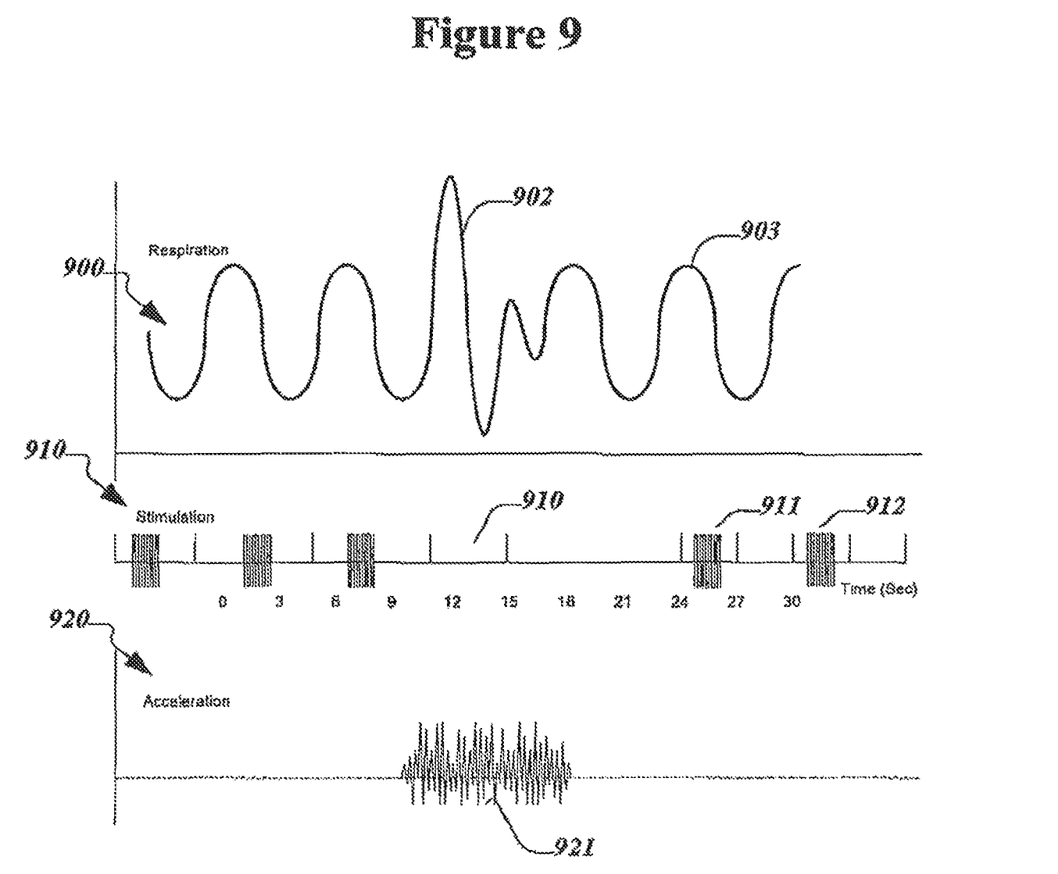
FIG. 9 is a schematic diagram showing physiologic data and signal artifact rejection.

FIG. 9 illustrates the rejection of an artifact caused by cough or motion during sleep. Respiratory signal 900 shows disturbed breath 902 caused by cough. This signal pattern can be recognized and rejected by identification of: an unacceptably fast inhalation slop, an unacceptably high amplitude, and/or the presence of a high frequency component in the respiratory signal spectrum. In all cases the stimulatory logic will reject this "breath" and not apply a stimulation burst 910. The next breath may also be rejected to allow the system to come to a stead state by extending the "blanking period" window to the duration of two normal breaths. After the normal pattern of breathing is restored 903, stimulation is resumed 911 and 912. In addition, implantable stimulator may be equipped with an accelerometer. Acceleration trace 920 shows high acceleration (vibrations) 921 corresponding to the patient's cough or motion. The acceleration signal may be used to reject a breath or several breaths and delay stimulation.

What is claimed is:

1. A method of prolonging a breath in a patient having a diaphragm innervated by a phrenic nerve and a vein near the phrenic nerve, the method comprising:
measuring respiration of the patient to find an inspiration phase of a natural, unstimulated breath; and
stimulating the phrenic nerve for a stimulation period, via a stimulation electrode located in the vein, starting proximate a peak of the inspiration phase with a stimulation magnitude that is sufficient to still the diaphragm and interrupt exhalation resulting in:
no significant lung volume change over a portion of the stimulation period; and
a trapping of air in at least one lung for the portion of the stimulation period, wherein the trapping reduces a breathing rate over the portion of the stimulation period, after which unstimulated exhalation of the air in the at least one lung occurs.

2. The method of claim 1 further characterized by said stimulating beginning at a time after the peak of the inspiration phase.

3. The method of claim 1 further comprising: repeating the measuring and stimulating steps for breaths over a period of time thus reducing an amount of air exchanged over the period of time.

4. The method of claim 1 wherein locating the stimulation electrode in the vein comprises implanting the stimulation electrode in a pericardiophrenic vein.

5. The method of claim 1 wherein prolonging the breath maintains a carbon dioxide concentration in the patient's blood above a threshold to prevent the onset of sleep disordered breathing.

6. A method of prolonging a breath in a patient having a diaphragm innervated by a phrenic nerve, a vein near the phrenic nerve and a lung associated with the phrenic nerve, the method comprising:
    measuring respiration of the patient to find an inspiration phase of a natural, unstimulated breath; and
    stimulating the phrenic nerve for a stimulation period exceeding an expiration phase duration of the natural, unstimulated breath, via a stimulation electrode located in the vein, starting proximate a peak of the inspiration phase, said stimulating interrupting exhalation, wherein there is no significant lung volume change in the lung and air is retained in the lung for a portion of the stimulation period, thereby reducing a breathing rate over the portion of the stimulation period, after which unstimulated exhalation of the retained air occurs, and wherein a capacity of the patient's body to regulate respiration is maintained.

7. The method of claim 6 further characterized by said stimulating beginning at a time after the peak of the inspiration phase.

8. The method of claim 6 further characterized by said stimulation period being sufficient to prevent apnea.

9. The method of claim 6 further comprising: repeating the measuring and stimulating steps for breaths over a period of time thus reducing an amount of air exchanged over the period of time.

10. The method of claim 6 wherein prolonging the breath maintains a carbon dioxide concentration in the patient's blood above a threshold to prevent the onset of sleep disordered breathing.

11. A method of reducing a breathing rate in a patient having a diaphragm innervated by a phrenic nerve and a vein near the phrenic nerve, the method comprising:
    measuring respiration of the patient to find an inspiration phase of a natural, unstimulated breath; and
    stimulating the phrenic nerve for a stimulation period, via a stimulation electrode in the vein, starting proximate a peak of the inspiration phase, with a stimulation magnitude that is sufficient to cause contraction of at least part of the diaphragm, resulting in trapped air in at least one lung and interrupting exhalation of the trapped air for a portion of the stimulation period, after which unstimulated exhalation of the trapped air occurs, said stimulation period being sufficient to reduce the breathing rate of the patient and reduce an amount of air exchanged by the at least one lung over the stimulation period while maintaining a capacity of the patient's body to regulate respiration.

12. The method of claim 11, further comprising a step of measuring an observed breathing rate without stimulation and then delivering stimulation pulses at a fixed stimulation rate that is less than the observed breathing rate.

13. The method of claim 11, further comprising a step of sensing motion or position of the patient and adjusting the stimulation magnitude based on the motion or the position of the patient.

14. The method of claim 11 wherein reducing the breathing rate maintains a carbon dioxide concentration in the patient's blood above a threshold to prevent the onset of sleep disordered breathing.

* * * * *

UNITED STATES PATENT AND TRADEMARK OFFICE
CERTIFICATE OF CORRECTION

PATENT NO. : 10,518,090 B2
APPLICATION NO. : 13/538713
DATED : December 31, 2019
INVENTOR(S) : Mark Gelfand et al.

It is certified that error appears in the above-identified patent and that said Letters Patent is hereby corrected as shown below:

On the Title Page

(57) Abstract
Delete "An implantable medical device for treating breathing disorders such as central sleep apnea wherein stimulation is provided to the phrenic never through a transvenous lead system with the stimulation beginning after inspiration to extend the duration of a breath and to hold the diaphragm in a contracted condition."
And insert -- An implantable medical device for treating breathing disorders such as central sleep apnea wherein stimulation is provided to the phrenic nerve through a transvenous lead system with the stimulation beginning after inspiration to extend the duration of a breath and to hold the diaphragm in a contracted condition. --

Signed and Sealed this
Sixth Day of August, 2024

Katherine Kelly Vidal
*Director of the United States Patent and Trademark Office*